Figure 1:
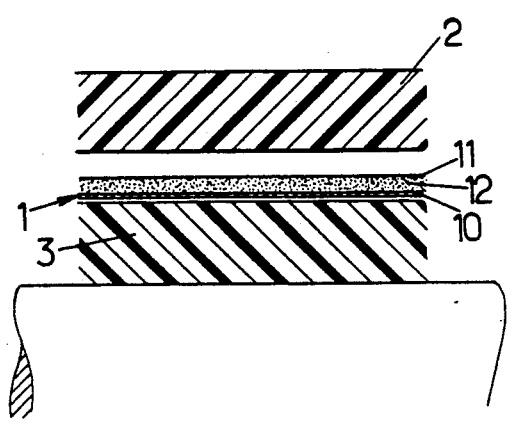

United States Patent [19]

Bottiglione et al.

[11] Patent Number: 5,246,770
[45] Date of Patent: Sep. 21, 1993

[54] COMPOSITE MATERIAL WHICH IS CAPABLE OF SWELLING IN THE PRESENCE OF WATER, SUPPORTS WHICH CAN BE USED FOR MANUFACTURE OF SAME AND USES THEREOF

[75] Inventors: Vincent Bottiglione, Hem; Gerard Mutschler, La Madeleine, both of France

[73] Assignee: Intissel S.A., France

[21] Appl. No.: 839,287

[22] Filed: Feb. 26, 1992

Related U.S. Application Data

[63] Continuation of Ser. No. 451,530, Dec. 18, 1989, abandoned.

[30] Foreign Application Priority Data

Dec. 20, 1988 [FR] France .................. 88.16837

[51] Int. Cl.⁵ .................. B23B 5/30; B23B 33/00; H01B 7/28; H01B 17/50
[52] U.S. Cl. .................. 428/244; 156/53; 156/276; 156/283; 156/320; 156/324; 174/23 C; 428/283; 428/286; 428/403; 428/913
[58] Field of Search .............. 174/23 C; 428/244, 283, 428/286, 403; 156/276, 283, 320, 324

[56] References Cited

U.S. PATENT DOCUMENTS

| | | | |
|---|---|---|---|
| 3,676,288 | 7/1972 | Hoyle | 428/283 |
| 4,250,172 | 2/1981 | Mutzenberg et al. | 428/283 |
| 4,381,782 | 5/1983 | Mazurak et al. | 428/283 |
| 4,413,995 | 11/1983 | Korpman | 428/283 |
| 4,758,466 | 7/1988 | Dabi et al. | 428/283 |
| 4,806,598 | 2/1989 | Morman | 428/283 |
| 4,820,560 | 4/1989 | Buchwald et al. | 428/244 |
| 4,828,911 | 5/1989 | Morman | 428/283 |
| 4,837,077 | 6/1989 | Anton et al. | 428/327 |
| 4,897,297 | 1/1990 | Zafiroglu | 428/283 |
| 4,902,559 | 2/1990 | Eschwey et al. | 428/283 |
| 4,965,129 | 10/1990 | Bair et al. | 428/240 |

FOREIGN PATENT DOCUMENTS 3639895 3/1988 Fed. Rep. of Germany ...... 428/283

*Primary Examiner*—James C. Cannon
*Attorney, Agent, or Firm*—Larson and Taylor

[57] ABSTRACT

The invention discloses a composite material 1 comprising essentially a mixture of hydroexpandable powder and thermobonding powder, sandwiched between two flat solid supports, one at least of which is at least partially hydrosoluble.

This material can be used in agriculture, medicine, surgery, in the hygiene field and in the cable, particularly electric cable, industry. In this application, when water penetrates into the cable, the at least partially hydrosoluble support or supports release the hydroexpandable powder which rapidly forms a pad preventing propagation of the water through the cable.

14 Claims, 1 Drawing Sheet

COMPOSITE MATERIAL WHICH IS CAPABLE OF SWELLING IN THE PRESENCE OF WATER, SUPPORTS WHICH CAN BE USED FOR MANUFACTURE OF SAME AND USES THEREOF

This application is a continuation of application Ser. No. 451,530 filed Dec. 18, 1989, now abandoned.

The invention relates to a composite material capable of swelling in the presence of water or an aqueous solution.

More precisely, the object of the invention is a composite "sandwich" type material, comprising essentially a mixture of hydroexpandable powder and thermobonding powder fixing two layers of identical or different materials one on the other, one at least of which is at least partially hydrosoluble, a material at least partially hydrosoluble for manufacturing this composite and the applications of this composite.

Composite materials are already known capable of swelling, without appreciable dissolution, in the presence of water. Such materials are generally used in the electric cable industry. In this case they are introduced, in the form of a ribbon, into the sheath of the cable to provide longitudinal sealing, by swelling and forming a plug if water penetrates accidentally into the cable not only at its ends but at a position where the sheath may be pierced, thus preventing the propagation of water inside the cable.

Among ribbons of this type may be mentioned the one commercialized by the firm Freundenberg, Weinheim, G.F.R. under the name VILEDON-FIBREX® and the references known up to date: K 3310, K 3312, K 3313, K 3303C and K 3002C, the one commercialized by the firm LANTOR, Veenendaal, Netherlands, under the references known to date: 3C 115, 3C 116, 3E 110, 3E 111, 3E 113, 3E 114, 3E 115 and 3E 116 to which reference is made in the patent FR 81 02863 and the one commercialized by the firm GECA TAPES, BAARLE NASSEAU, NETHERLANDS, under the references known to date: GT 100, GT 101, GT 200, GT 201, GT 1000, GT 205.

These ribbons are essentially formed of a hydroexpandable polymer powder sandwiched between two conventional non-woven fabric layers.

Cohesion of the composite is obtained by incorporating a thermoplastic substance (powder, fibre or other) in the hydroexpandable polymer powder. Under the combined action of pressure and heat, the thermoplastic substance softens, becomes sticky and thus provides cohesion of the composite.

During this bonding action, the nature of the non-woven fabrics and their association with the thermobonding substance cause an unfavourable effect: in fact, the two non-woven fabric layers are firmly and durably bonded together by the molten thermoplastic powder mass. This limits the swelling of the hydroexpandable polymer in the presence of water or an aqueous solution.

According to the invention, it has now been discovered that the properties of such a composite material could be considerably increased by replacing one at least of the two conventional non-woven fabric layers by one or two flat solid supports, partially or completely soluble in water or aqueous solutions (hereafter to simplify: water).

Among other things an object of the invention is the composite material thus obtained.

The invention relates more particularly to a composite material comprising essentially a mixture of hydroexpandable powder and thermobonding powder, sandwiched between two solid flat supports, one at least of which is at least partially hydrosoluble.

In a preferred embodiment, said mixture is formed of:
80 to 60% by weight of hydroexpandable powder, and
20 to 40% by weight of thermobonding powder.

Such a material allows the water to be held at the position where it is introduced and thus has numerous applications.

Thus, it may be used as a sealing ribbon in cables, particularly electric or telecommunications cables, but also as germination activator or for the transplantation of young shoots, in medicine or surgery as "sponge", or in the field of hygiene, for example in disposable nappies.

The supports and in particular the at least partially hydrosoluble support or supports of this material are chosen essentially as a function of the final use thereof.

They may be formed particularly of a non-woven fabric, a textile, paper, or a synthetic film. For most applications, particularly in the energy transporting and telecommunications cable industry, they are preferably flexible.

The hydroexpandable polymer may be formed from any polymer or mixture of polymers compatible with the support and the final use thereof and capable of considerable swelling in the presence of water or of aqueous solutions by "storing" them, yet insoluble therein, i.e. having a solubility in these liquids less than 5%.

Advantageously, the hydroexpandable polymer is chosen so that it is capable of absorbing at least 15 times its own weight of water.

The hydroexpandable polymer may be chosen particularly from modified acrylic polymers, grafted starches, polyacrylamides, carboxymethylcellulose and its derivatives and advantageously generally from polymers corresponding to the definition of "superabsorbents", namely polymers which are "insoluble" (in the above mentioned meaning) in the fluids which they absorb and absorbing at least 15 times their own weight of water or of aqueous solution.

As superabsorbent polymers, there may be mentioned by way of indication but in no wise limiting:
  the acrylic polymer commercialized by the firm JAPAN CATALYTIC CHEMICAL under the name AQUALIC®,
  the acrylamide polymer commercialized by the firm CYANIMID under the name HYDROBLOCK®,
  the carboxymethylcellulose polymer commercialized by the firm HERCULES under the name AQUASORB®,
  the starch/polyacrylic acid polymer obtained by grafting and commercialized by the firm LION under the name LION-POLYMER®, and
  the sodium polyacrylate polymer commercialized by the firm GRAIN PROCESSING under the name WATER-LOCK J®.

The thermobonding powder is chosen from the thermoplastic polymers capable of bonding two fibrous or solid surfaces together and compatible with the other materials used and for the contemplated use.

Among the thermobonding polymer powders which may be advantageously used in the scope of the invention, there may be mentioned by way of non limitative examples:
- the polyethylenes commercialized by the firm CDF CHIMIE under the trademark LOTRENE ®,
- the polyethylenes commercialized by the firm EXXON under the trademark ESCORENE ®, and
- the polyamides commercialized by the firm EMS under the trademark GRILTEX ®.

For use as sealing agent in the industry manufacturing electric cables for transporting medium and high voltage energy, it is advantageous to make the composite material electrically conducting, so as to obtain acceptable conductivity in its thickness and on the surface.

To achieve this, at least one of the two flat solid supports is charged previously with a material for obtaining surface and transverse resistance adapted to the type of cable manufactured. In general, for this, 5 to 20 g/m² of conducting carbon black is introduced into said support or each of said supports during manufacture thereof.

Conducting carbon black may also be introduced into the hydroexpandable powder and the thermobonding powder mixture in proportions such that a distribution of 8 to 20 g/m² of carbon black is obtained in the sandwiched mixture.

In a preferred embodiment of the invention, a composite material is thus obtained comprising essentially a mixture of 80 to 60% by weight of hydroexpandable powder and 20 to 40% by weight of thermobonding powder, sandwiched between two flat solid supports, one at least of which is at least partially hydrosoluble and 5 to 60 g/m² of conducting carbon black.

The composite material according to the invention may be produced in a way known per se by sprinkling, on a flat solid support, the hydroexpandable powder and thermobonding powder mixture containing, if required, conducting carbon black. This assembly is then heated to a sufficient temperature to cause the thermobonding powder to melt. Such heating may be carried out in a drier, an oven, for example a pulsed hot air oven, or under infrared heating ramps. The second flat solid support is then applied and pressed on the heated assembly by means of rollers.

This assembly may also be formed directly by means of two heated rollers (calender).

In an advantageous embodiment, at least one of the supports of the composite of the invention is formed of a partially hydrosoluble non-woven fabric. Non-woven fabrics of this type are new.

The invention has further as object a partially hydrosoluble non-woven fabric which may be used for manufacturing the composite material of the invention, characterized in that it essentially comprises by weight:
- 95 to 55% of non hydrosoluble fibres;
- 5 to 35% of hydrosoluble binder; and
- 0 to 10% of surface-active agent.

Such a non-woven fabric may further comprise conducting carbon black, particularly for use in electric cables.

A further object of the invention, in an advantageous embodiment, is a partially hydrosoluble non-woven fabric characterized in that it essentially comprises by weight:
- 76 to 28% of non hydrosoluble fibres;
- 4 to 18% of hydrosoluble binder;
- 0 to 4% of surface-active agent; and
- 20 to 50% of conducting carbon black.

The non hydrosoluble fibres may be natural, artificial or synthetic. They may be viscose fibres, polyester fibres, acrylic fibres or mixtures of such fibres.

As examples of such fibres may be mentioned, purely by way of illustration,:
- the polyester fibres commercialized by the firm EMS, under the tradename GRILENE ®;
- the polyester fibres commercialized by the firm DU PONT DE NEMOURS under the tradename DACRON ®;
- the polyamide fibres commercialized by the firm EMS under the name GRILON ®;
- the polypropylene fibres commercialized by the firm STEEN under the name POLYSTEEN ®; and
- the viscose fibres commercialized by the firm LENZING.

The hydrosoluble binder is chosen from the hydrosoluble binders capable of fixing flat fibrous masses, without substantially modifying their physico-chemical properties.

Among binders of this type which may be advantageously used in the scope of the invention, may be mentioned by way of non limitative examples:
- the polyvinylpyrrolidones commercialized by the firm GAF, under the tradenames PVP K 30 ® and PVP K 90 ®;
- the polyvinylpyrrolidones and vinylpyrrolidone-vinyl acetate copolymers commercialized by the firm BASF (GFR) under the tradenames of LUVISKOL K30-K90 ®; and
- the hydropropylcelluloses commercialized by the firm HERCULES (USA) under the tradenames KLUCEL H, M, G, J, L and E ®.

Although the presence of a surface-active agent is not indispensable, it has been discovered that it plays a favorable role, particularly in the distribution of the binder during manufacture of the non-woven fabric.

Preferably an anionic or non ionic surface-active agent is used as surface-active agent.

Among the surface-active agents which may be used within the scope of the invention there may be mentioned by way of non limitative examples:
- the product commercialized by the firm ROHM AND HAAS (USA) under the tradenames of TRITON X 100 ® and TRITON GR 5 M ®;
- the product commercialized by the firm BYKMAL-LINCKRODT under the name ANTI-TERRA-U ®;
- the product commercialized by the firm PETRO-CHEMICALS CO., INC. under the name of MORWET EFN ®;
- the products commercialized by the firm AIR PRODUCTS under the name SURFYNOL ®; and
- the product commercialized by the firm BASF (GFR) under the name LEOPHEN RA ®.

Such a partially hydrosoluble non-woven fabric may be manufactured conventionally using the so-called "dry process". This process consists of an operation for carding the fibres, to make these fibres parallel with each other and produce an homogeneous layer. This layer is then fixed by means of the hydrosoluble binder, used for example in the form of an aqueous phase solution whose concentration is dosed so as to obtain a sufficiently strong non-woven fabric for the application contemplated, while permitting the most rapid dissolution possible when the complex plays its role in contact with water or an aqueous solution.

This concentration depends particularly on the nature and on the physical characteristics of the fibres to be bonded together and on the binder used. In most cases it may be from 3 to 20%, advantageously 7%. The hydrosoluble binder solution is deposited on the layer, for example in the form of foam using a device known as a "foamer".

Possible additives (such as surface-active agent, conducting carbon black) may be incorporated in the solution before or during foaming.

The layer thus impregnated is then dried, for example using a rotary through air drier, a system of heated rollers, called "maniques", a heating tunnel or any other device suitable for this application.

The non-woven fabric may then be either wound for subsequent use or fed immediately into the manufacturing process of the composite of the invention.

In another advantageous embodiment, at least one of the supports of the composite of the invention is formed from a non-woven fabric, at least partially hydrosoluble, formed wholly or partially of fibres which are at least partially hydrosoluble and thermobonding, the bonding of the fibres being then achieved by heat bonding.

In this context, by way of example, the non-woven may be formed of:
50 to 100% of PVA (polyvinyl alcohol fibres; and
50 to 0% of natural, artificial or synthetic fibres, such for example as those mentioned above by way of examples.

As PVA fibres, those commercialized by the firm KURARAY under the trademark KURALON ® may be mentioned.

In yet another embodiment, the composite of the invention may comprise as support at least one textile, at least partially hydrosoluble which is woven or knitted.

As new textile of this type may be mentioned a woven or knitted textile, at least partially hydrosoluble, which is essentially formed of:
50 to 100% of PVA (polyvinyl alcohol) threads,
50 to 0% of conventional natural, artificial or synthetic threads, obtained for example from the fibres mentioned above by way of examples.

The paper, at least partially hydrosoluble, which may also be used as support in the composite of the invention may be formed conventionally by dispersing natural, artificial or synthetic fibres in a bath with a high concentration of hydrosoluble binder.

As paper of this type, may be mentioned the paper commercialized by the firm NEDI (France) under the name "Hydro dispersable paper".

As hydrosoluble support film a synthetic polyvinyl alcohol film may be used. In this context, the films commercialized by the firm NEDI (France) under the name NEDOL ® may be mentioned.

As was indicated above, the composite material of the invention may have various uses.

Thus, it may be used as water or physiological liquid absorbent, particularly in medicine and surgery or in the field of sanitary products such as disposable nappies, etc.

It may in particular be incorporated in the manufacture of nappies for babies, in the form of strips or cut pieces, thus reinforcing absorption and urine retention, especially at particular positions depending on the morphology of the babies.

The composite of the invention may also be used in agriculture as germination activator for holding water at the position where the grain is deposited: such precise localization is particularly interesting when the water is enriched with growth promoting substances, such as nutritional substances. In addition, substances such as anticryptogamic compounds, fungicides, fertilizers may be readily incorporated in the composite material at the time of powdering.

The composite material of the invention may also be used for the transplantation of young shoots. They are packed with their clod of earth in the composite material and may be transplanted without risk after soaking in water.

As mentioned above, another important application of the composite material of the invention is its use in cables for providing longitudinal sealing thereof.

In the case of contact with water, one at least of the two supports is decomposed, at least partially, uncovering the hydrophilic sites of the hydroexpandable polymer.

The result is compact and rapid swelling. At the same time, the hydroexpandable polymer is released by decomposition of the support or supports. Such release allows displacement of the gel which may be oriented towards the zones of preferential passage of the water, thus providing excellent efficiency in situ.

Figure 2:
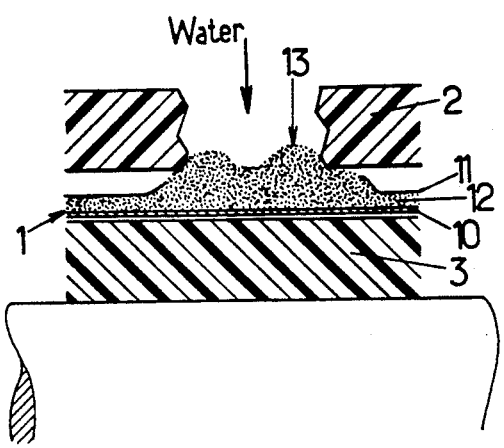

Referring to FIGS. 1 and 2 of the accompanying drawings, the behaviour of the composite material of the invention will be described hereafter when it is incorporated in the sheath of a cable, in the presence of water passing accidentally through the external sheath of the cable.

The composite material of the invention 1, formed of two flat solid supports 10 and 11, one 11 at least of which is completely or partially hydrosoluble, bonded together by a mixture 12 of hydroexpandable polymer powder and thermobonding polymer powder, is placed between the external sheath 2 and the core, or more generally the internal sheath 3 of the cable. Because of the construction of the cable, its parts 2 and 3 are often separated by a slight empty space. In addition, they move away from each other to a greater or lesser extent during use of the cable (FIG. 1).

If water penetrates accidentally into the cable (FIG. 2) through the external sheath 2 and passes through the flat solid support 11, which is at least partially hydrosoluble, of the composite material 1, it dissolves this flat and solid support at least partially and practically instantaneously and enters into contact with the hydroexpandable polymer powder, about the position at which it penetrated into the cable.

The hydroexpandable polymer which was held between the two supports is then released at this position and thus has the possibility of moving, while gelling, so as to form about the water penetration zone a pad 13 which prevents propagation of the water in the cable.

The hydroexpandable polymer which is no longer a prisoner of the supports may develop all its swelling capacity for blocking the accidental entry of water into the cable. Such capacity and such rapidity are improved with respect to the prior art where the hydroexpansion force must first of all unstick the two non hydrosoluble supports, between which the gel remained prisoner for an appreciable period of time.

In addition, with the composite of the invention 1, the gel created is completely efficient for it is free and accumulates close to the infiltration zone.

It is obvious that such a description is only given by way of illustration and that in particular other arrangements could be provided inside the cable without departing from the scope of the invention.

Figure 3:
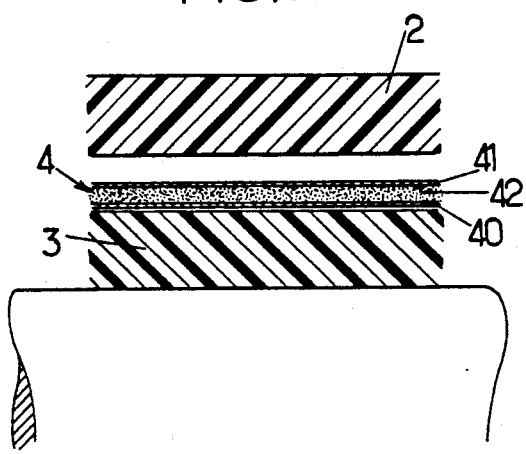
Figure 4:
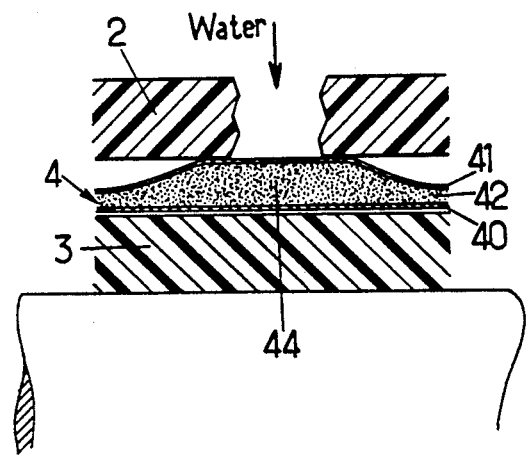

FIGS. 3 and 4 show what happens when prior art composites such as defined above are used.

The composite material 4 is formed of a layer of a mixture 42 of a hydroexpandable polymer and a thermoplastic substance sandwiched between two non hydrosoluble non-woven fabric layers 40 and 41. When water penetrates accidentally into the cable, the hydroexpandable polymer swells, at the point of penetration of the water, without being separated from the supports: it causes "swelling" 43 just at this level, but cannot form a pad about this zone.

The protection conferred is therefore less efficient than with the invention and, since this polymer cannot develop all its swelling capacity, particularly because of the strong and durable bond between the two non hydrosoluble supports due to the thermoplastic polymer, it is necessary to use a larger amount.

The following examples are given to better illustrate and explain the invention without however limiting the scope thereof.

EXAMPLE 1

PARTIALLY HYDROSOLUBLE NON-WOVEN FABRIC HAVING A CONVENTIONAL NON HYDROSOLUBLE FIBRE BASIS

| | |
|---|---|
| Polyester fibres GRILENE ® HTB of the firm EMS (Switzerland) | 73% by weight |
| Polyvinylpyrrolidone binder PVP K30 ® from the firm GAF (USA) | 25% by weight |
| Wetting agent TRITON GR 5 M ® from the firm ROHM AND HAAS (USA) | 2% by weight |

EXAMPLE 2

MANUFACTURE OF A PARTIALLY HYDROSOLUBLE NON-WOVEN FABRIC COMPRISING THERMOBONDING HYDROSOLUBLE FIBRES.

| | |
|---|---|
| KURALON ® PVA fibres from the firm KURARAY (Japan) | 70% by weight |
| Polyester GRILENE HTB ® fibres from the firm EMS (Switzerland) | 30% by weight |

The fibre layer is damped then heat bonded by calendering.

EXAMPLE 3

MANUFACTURE OF A COMPOSITE MATERIAL ACCORDING TO THE INVENTION

| COMPONENTS | WEIGHT |
|---|---|
| Non woven non hydrosoluble support Ref: 42040 from INTISSEL (France) | 40 g/m$^2$ |
| Hydroexpandable powder ref: 10 SHP from NORSOLOR (France) | 35 g/m$^2$ |
| Thermoplastic polyethylene powder ESCORENE ®, ref: MP 654 from EXXON (USA) | 10 g/m$^2$ |

-continued

| COMPONENTS | WEIGHT |
|---|---|
| Non woven fabric support, at least partially hydrosoluble, according to the invention (in particular with the compositions described above and particularly in examples 1 and 2) | 15 g/m$^2$ |

The non hydrosoluble support is a conventional non-woven fabric, which may be conducting or not, manufactured using the so-called "dry process", from polyester fibres and a butadiene acrylonitrile binder, charged or not with conducting carbon black. These fibres are oriented preferably parallel.

On this non woven non hydrosoluble support is then deposited the hydroexpandable powder and thermobonding powder mixture using a sprinkler formed of a powder storage tank at the bottom of which is situated an engraved roller which delivers the powder and whose speed of rotation determines the weight of powder deposited. It is in this example 45 g/m$^2$.

The powdered non hydrosoluble non-woven fabric support then enters an oven comprising infrared radiation ramps, adjusted to a sufficient temperature to cause the thermobonding powder to melt.

On leaving this oven, the at least partially hydrosoluble non-woven fabric support, which is conducting or not, is unwound and applied with pressure to the first powdered support by means of two rollers whose pressure force may be adjusted.

What is claimed is:

1. A method for manufacturing a composite material capable of swelling in the presence of water, comprising selecting a first and a second flat solid support, at least one of which is partially or completely soluble in water, and a mixture of hydroexpandable powder and thermobonding powder, sprinkling the said mixture on the said first support thus obtaining an assembly comprising the said support and thereon the said mixture, heating the said assembly to cause the thermobonding powder to melt, and applying the said second flat solid support on the heated assembly.

2. The method according to claim 1, wherein the mixture is consisting of:
   80 to 60% by weight of hydroexpandable powder; and
   20 to 40% by weight of thermobonding powder.

3. The method according to claim 1, wherein the solid supports, which may be identical or different, are consisting of a non-woven fabric, a textile, a paper or a synthetic film.

4. The method according to claim 1, wherein the solid supports are flexible.

5. The method according to claim 1, wherein the hydroexpandable powder is a superabsorbent.

6. The method according to claim 1, wherein the composite material is electrically conducting.

7. The method according to claim 6, wherein at least one of the supports contains from 5 to 20 g/m$^2$ of conducting carbon black.

8. The method according to claim 6, wherein the said mixtures comprises from 8 to 20 g/m$^2$ of conducting carbon black.

9. Composite material obtained by the method according to claim 1.

10. Composite material obtained by the method according to claim 1 and comprising a mixture consisting essentially of from 80 to 60% by weight of hydroexpandable powder and from 20 to 40% by weight of thermobonding powder, two flat solid supports, between which the said mixture is sandwiched and at least one of which is partially or completely soluble in water, and from 5 to 60 g/m² of conducting carbon black.

11. Non-woven fabric partially soluble in water usable as flat solid support in the method according to claim 1, and consisting essentially by weight of:
   95 to 55% of non hydrosoluble fibers;
   5 to 35% of hydrosoluble binder; and
   0 to 10% of surface-active agent.

12. Non-woven fabric partially soluble in water usable as flat solid support in the method according to claim 1, consisting essentially by weight of:
   76 to 28% of non hydrosoluble fibers;
   4 to 18% of hydrosoluble binder;
   0 to 4% of surface-active agent; and
   20 to 50% of conducting carbon black.

13. Non-woven fabric partially or completely soluble in water usable as flat solid support in the method according to claim 1, characterized in that it is formed, wholly or partially, of hydrosoluble and thermobonding fibers and that the bonding of the fibers is provided by heat bonding.

14. Flat solid support, which is partially or completely soluble in water usable in the method according to claim 1, characterized in that it is woven or knitted.

* * * * *